United States Patent [19]

Studdert

[11] Patent Number: 5,084,271

[45] Date of Patent: Jan. 28, 1992

[54] VACCINE FOR EQUINE HERPESVIRUS

[76] Inventor: Michael J. Studdert, 13 Highland Ave., Balwyn, Victoria 3103, Australia

[21] Appl. No.: 221,640

[22] Filed: Jul. 8, 1988

Related U.S. Application Data

[63] Continuation of Ser. No. 785,661, Oct. 9, 1985, abandoned.

[30] Foreign Application Priority Data

Sep. 11, 1984 [AU] Australia ............... PG8064

[51] Int. Cl.$^5$ ............ A61K 39/23; A61K 39/245; A61K 39/17; A61K 39/295
[52] U.S. Cl. ....................................... 424/89
[58] Field of Search ........................... 424/89

[56] References Cited

U.S. PATENT DOCUMENTS

| | | | |
|---|---|---|---|
| 4,083,958 | 12/1977 | Bryans | 424/89 |
| 4,525,349 | 6/1985 | Montagnon et al. | 424/89 |
| 4,537,768 | 8/1985 | Apontoweil et al. | 424/89 |

OTHER PUBLICATIONS

Allen and Bryans, *Progress in Veterinary Microbiology and Immunology*, 2, 78-144 (1986).
Studdert, *Science*, 214, 562-564 (1981).
Burrows and Goodridge, *Proceeding of the Third International Conference on Equine Infectious Diseases*, 1973, pp. 306-321.
Burrows and Goodridge, *Journal of Reproduction and Fertility*, Supplement 23, pp. 661-715 (1975).
Studdert and Blackney, *Australian Veterinary Journal*, 55, 488-492 (1978).
Thompson et al., *Veterinary Microbiology*, 4, 209-222 (1979).
Kawakami and Shimizu, *Proceedings of the Fourth International Conference on Equine Infectious Diseases*, 1978, pp. 75-82.
Horner, *New Zealand Veterinary Journal*, 29, 7-8 (1981).
Sabine et al., *Equine Veterinary Journal*, 15, 366-370 (1983).
*Veterinary of Virology*, Academic Press, pp. 265-266.
Campbell and Studdert, *Veterinary Bulletin of Commonwealth Bureau of Animal Health*, Fed. 1983 (pp. 135-146).
Studdert, *Letter to the Editor: Fetal and Respiratory Stains of Equine Herpes Virus Type I* (6-7-83).
Studdert, *Letter to the Editor: Vaccines for Equine Herpes Virus Type I* (1983).

*Primary Examiner*—Nathan M. Nutter

[57] ABSTRACT

A vaccine for equine herpesvirus which includes the equine rhinopneumonitis virus (equine herpesvirus) type 4 (EHV-4) in an inactivated or modified live virus form.

Also disclosed is a combined vaccine based on the equine abortion virus (e.g. herpesvirus type 1 (EHV-1)) and equine rhinopneumonitis virus (equine herpesvirus type 1 (EHV-1)) and equine rhinopneumonitis virus (equine herpesvirus type 4 (EHV-4)) in an inactivated or modified live virus form.

The viruses are present in a suitable adjuvant with a suitable preservative.

7 Claims, 3 Drawing Sheets

VACCINE FOR EQUINE HERPESVIRUS

This is a continuation of application Ser. No. 785,661, filed Oct. 9, 1985 now abandoned.

FIELD OF THE INVENTION

This invention relates to vaccines for the protection of horses against the diseases caused by equine herpes viruses.

BACKGROUND OF THE INVENTION

Equine abortion and equine rhinopneumonitis are commonly recognized diseases attributed to equine herpesvirus type 1 (EHV-1). Evidence has accumulated indicating that two distinct viruses are involved one predominantly causing abortion, and the other, predominantly causing rhinopneumonitis. The viruses are distinct in their epizootiology, pathogenicity for mice, growth characteristics in cell culture, virus neutralization, restriction endonuclease DNA fingerprints, and viral proteins and by DNA:DNA hybridization the viruses have <20% homology.

The EHV-1 predominantly associated with abortion has been designated subtype 1 or fetal (F) strain, and the EHV-1 predominantly associated with rhinopneumonitis has been designated subtype 2 or respiratory (R) strain. The differences in restriction endonuclease DNA fingerprints led to a proposal that the viruses be designated EHV-1 and EHV-4 for the agents of abortion and of rhinopneumonitis, respectively; this has been agreed to in general. Although the designations EHV-1 and EHV-4 recognize the important molecular differences at the DNA level, they do not remove all of the ambiguities. It is assumed that EHV-1 is acquired as a respiratory tract infective agent and may cause respiratory tract disease; yet, reported isolations of EHV-1 from naturally occurring cases of respiratory tract diseases are few. Conversely, there are five recorded isolations of EHV-4 from aborted fetuses.

Definition of the immunologic relationships between EHV-1 and EHV-4 is central to the control of diseases caused by the two viruses. The present inventor has more clearly determined the immunological relationship between EHV-1 and EHV-4 by in vitro lymphocyte blastogenesis in specific-pathogen-free (SPF) foals, and by virus neutralization, using antisera produced in rabbits and SPF foals.

SUMMARY OF THE INVENTION

It is the object of the present invention to provide an improved vaccine specific to equine rhinopneumonitis virus and to provide a combined vaccine specific to both equine abortion virus and equine rhinopneumonitis virus.

In one form, the invention provides a vaccine based on the equine rhinopneumonitis virus (equine herpesvirus) type 4 (EHV-4) in an inactivated or modified live virus form.

In another form, the invention provides a combined vaccine based on the equine abortion virus (equine herpesvirus type 1 (EHV-1)) and equine rhinopneumonitis virus (equine herpesvirus type 4 (EHV-4)) in an inactivated or modified live virus form.

In one form EHV-1 and EHV-4 are present in the vaccine in equal proportions, for example. 1 ml of each, in an aluminium hydroxide adjuvant plus a suitable preservative.

The strains of virus are preferably specially selected, high-yielding strains originally isolated in the applicant's laboratory and selected from a large number of other similar viruses. The respective preferred strains are EHV-1 strain 438/77 and EHV-4 strain 405/76 viable strains of which have been deposited with the American Type Culture Collection, Rockville, Md. with accession numbers VR2229 and VR2230, respectively. The titer of both these viruses is greater than $10^{7.5}$ plaque forming units per ml. Of course it will be appreciated that other strains of EHV-1 and EHV-4 may be used with similar results.

One preferred method of preparing each vaccine includes the steps of growing the selected strain of EHV-4 in an equine dermis cell or other appropriate cell line, inactivating the virus and combining the virus with a suitable adjuvant and preservative. In the case of the combined virus vaccine, EHV-1 is prepared by growing the selected strain of EHV-1 in an equine dermis cell line, or other appropriate cell line inactivating the virus and combining the inactivated virus with the inactivated EHV-4 virus together with a suitable adjuvant and preservative. Inactivation of the viruses may be achieved by the use of 0.2% beta propiolactone for 24 hours at 4° C.

The EHV-4 vaccine or the combined EHV-1 and EHV-4 vaccine is administered to horses by intramuscular injection with, initially, two doses given one month apart, then, booster vaccinations every six to twelve months. Pregnant mares are vaccinated every two months throughout pregnancy.

DESCRIPTION OF PREFERRED EMBODIMENTS

The following description provides preliminary data on the immunologic relationship between EHV-1 and EHV-4 which led to the realization that a vaccine based on EHV-4 would be most useful and that a combined vaccine based on EHV-1 and EHV-4 would more effectively control diseases caused by both viruses than the presently used monovalant vaccines based on EHV-1 alone.

Equine fetal kidney (EFK) cells were used at 5th passage. Virus strains 438/77 and 405/76 were used as representatives of EHV-1 and EHV-4, respectively. Their origin, initial passage history, and typing have been described at pages 488 to 492 of the Australian Veterinary Journal Vol. 55 1979 and at pages 249-259 of Archives of Virology Vol. 77 1983.

Monolayers of EFK cells in 1,200 cm² roller bottles were inoculated at a multiplicity of infection of 1 with either EHV-1 or EHV-4. Serum-free maintenance medium was added after adsorption. When cytopathic changes in the monolayers were complete, the roller bottles were frozen and thawed three times, the contents were clarified by low-speed centrifugation, and the supernatants were harvested and stored at $-70°$ C. Titers of these virus stocks were measured by plaque assay. The titer of the EHV-1 stock was $5 \times 10^6$ plaque-forming units (PFU)/ml, and that of the EHV-4 stock was $7.5 \times 10^6$ PFU/ml, although titers $>10^{7.5}$ are now being evaluated.

Virus stocks were inactivated by treatment with 0.2%-propiolactone (BPL) for 27 hours at 4° C. and then for three hours at 37° C. to hydrolyze residual BPL. Complete inactivation of infectivity was verified by three passages (approximately seven days/passage) of 0.4 ml of inoculum in EFK cells.

Inactivated virus stocks were concentrated five times by ultrafiltration through a membrane system at 4° C. and 400 kPa. Concentration was verified by protein estimation and particle counts. Roller bottles of noninfected EFK cell monolayers were similarly processed to produce control cell lysate antigen (CL Ag). Each antigen was dispensed in 2-ml aliquotes and stored at $-70°$ C.

Three colostrum-deprived SPF foals were used. Foals were removed immediately after induced parturition or supervised natural birth and then transferred to an isolation unit where they were reared under SPF conditions. Freedom from infection with EHV-1 and EHV-4 was established before the foals were vaccinated by the absence of clinical signs of respiratory tract disease and the lack of detectable (titer <8) virus-neutralizing antibody (VN Ab) against EHV-1 and EHV-4. During the vaccination period, foal 2 remained free of clinical respiratory tract disease and detectable VN Ab to EHV-1 and EHV-4.

Foals 1, 2 and 3 were 5, 4 and 10 weeks old, respectively, on the day of the first vaccination dose was given (day 0). The foals were vaccinated and challenge exposed according to the schedule in Table 1.

Vaccinations given on days 0 and 14 comprised IM injections of 2 ml of antigen gently mixed with 0.5 ml of steril Alhydrogel (approx. 17 mg of aluminum hydroxide/ml). Before challenge exposure with EHV-1, foals 1 and 2 were separated from foal 3 by transfer to another isolation unit.

Intranasal (IN) challenge exposures were conducted by swabbing the nasal and nasapharyngeal mucosa with virus diluted in 5 ml of maintenance medium (Table 1).

Rectal temperatures and presence or absence of signs of respiratory tract disease were monitored twice daily. Blood samples for total and differential WBC counts and for lymphocyte blastogenesis (LB) assays and nasal swabs and blood samples for virologic examination were obtained twice a week, except that these collections were done three times in the first week after virus challenge exposures. Serum samples for VN Ab assay were obtained twice a week.

Total and differential WBC counts were measured by standard procedures. Nasal swabs were transported (4° C.) in 5 ml of maintenance medium and filtered through a 450 nm (APD) membrane filter before inoculation onto EFK cells. Some swabs were frozen at $-70°$ C. before filtration and inoculation at a later date.

The WBC from heparinized blood samples (10 IU of heparin/ml of blood were examined for infective virus. Several processing techniques were attempted, including (i) inoculation of fresh or freeze/thaw-disrupted buffy coat cells onto EFK cells, (ii) inoculation of fresh or freeze/thaw-disrupted mononuclear cells (separated from blood by Ficoll-diatrizoate density gradient centrifugation) onto EFK cells, and (iii) inoculation of mitogen stimulated mononuclear cells onto EFK cells. All nasal swabs and WBC samples were passaged three times on EFK cells with seven days/passage to detect viral cytopathic effects. Positive samples were typed by plaque morphology analysis and restriction endonuclease fingerprinting of virus DNA.

For LB assays, separated triple-washed mononuclear cells were suspended in RPM1 1640 medium supplemented with 2 nm L-glutamine, 3 nm Hepes buffer, penicillin (40 U/ml), streptomycin (40 g/ml), amphotericin b (1 g/ml), and SPF foal serum. Two batches of SPF foal serum were used: serum A for mononuclear cells from foals 1 and 2 and serum B for mononuclear cells from foal 3. The medium was supplemented with either 15% serum A or 10% serum B: concentrations which elicited optimum LB responses during preliminary tests. Mononuclear cells were suspended in supplemented RPM1 1640 medium at 2 concentrations: $1 \times 10^6$ cells/ml and $5 \times 10^5$ cells/ml. Viability was assessed by trypan blue exclusion, and purity was assessed by examination of stained smears.

Six wells of a round-bottomed tissue culture multiwell plate, each containing 0.025 ml of 1 of the following were prepared: RPM1 1640 medium: 0.31 g phytohemagglutinin; 1:2 dilutions of EHV-1 antigen (EHV-1 Ag), EHV-4 AG and CL Ag; 1:5 dilutions of EHV-1 Ag, EHV-4 Ag and CL Ag; 1:10 dilutions of EHV-1 Ag, EHV-4 Ag and CL Ag; and 1:20 dilutions of EHV-1 Ag, EHV-4 Ag and CL Ag. Mononuclear cells $(2 \times 10^5$ and $1 \times 10^5)$ in 0.2 ml of medium were added to triplicate wells of each Ag or mitogen.

Preliminary results elicited optimum LB response with $2 \times 10^5$ mononuclear cells/well plus 1:5 dilution of each Ag, and the range of variables (in the preceding paragraph) was chosen to allow for changes in the immunologic status of the foals, with respect to EHV-1 and EHV-4, during the vaccinations and challenge exposures.

Mitogen cultures were incubated for three days and Ag cultures, for four days, at 37° C. in a humidified 5% $CO_2$ atmosphere. All cultures were pulsed with 1 Ci[$^3$H]thymidine, during the last 18 to 20 hours of the incubation. At the end of incubation, cultures were harvested with a semiautomated cell harvester onto glass fiber filter paper, transferred to plastic scintillation vials, and processed for scintillation counting by addition of 0.5 ml of tissue solubilizer, 0.02 ml of glacial acetic acid, and 2.5 ml of scintillation fluid. Scintillations were counted for one minute in a liquid scintillation counter and expressed for each well as counts per minute (cpm) minus background cpm.

The cpm of wells incubated with RPMI 1640 medium (nonstimulated wells) and mitogen (stimulated wells) were used to verify the presence of functional mononuclear cells.

Stimulation indices (SI) were calculated for each dilution of Ag. e.g., SI for 1:2 dilution of EHV-1 Ag=-mean cpm 1:2 dilution of EHV-1 Ag stimulated wells/-mean cpm 1:2 dilution CL Ag-stimulated wells. The highest of the 8 SI (4 Ag dilutions and 2 cell concentrations) was taken as the peak response for a particular day.

Serum samples were heat inactivated (56° C. for 30 minutes) and tested for VN Ab to EHV-1 and EHV-4 by a microprocedure.

Rabbits were inoculated IM with 1 ml of stock virus (emulsified in 1 ml of Freund's complete adjuvant) at 8, 10, and 12 weeks of age, and then IV with 1 ml of stock virus at 14, 16 and 17 weeks of age. Blood was collected 10 days after the last injection; serum was prepared, heat inactivated, and tested for VN Ab to both EHV-1 and EHV-4.

Clinical signs of respiratory tract disease were not observed in any of the foals after vaccination or challenge exposure.

Figure 1:
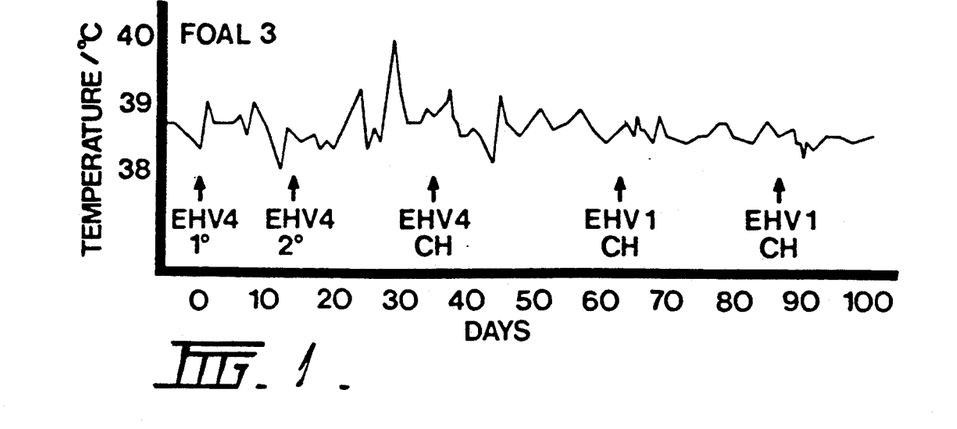
FIG. 1 is a temperature chart for foal 3 after administration of inactivated EHV-4 antigen with adjuvant on days 0 and 14, challenge exposure with live EHV-4 on day 35, and challenge exposure with live EHV-1 on days 63 and 87.

The temperature chart for foal 3 (FIG. 1) is typical of the responses of the foals. Rectal temperatures did not exceed 40° C. and fluctuations associated with vaccination or challenge exposures were small (approximately 0.5°). The temperature or 39.9° C. on day 29 in foal 3 was associated with the development of a small facial swelling of undetermined origin.

Figure 2:
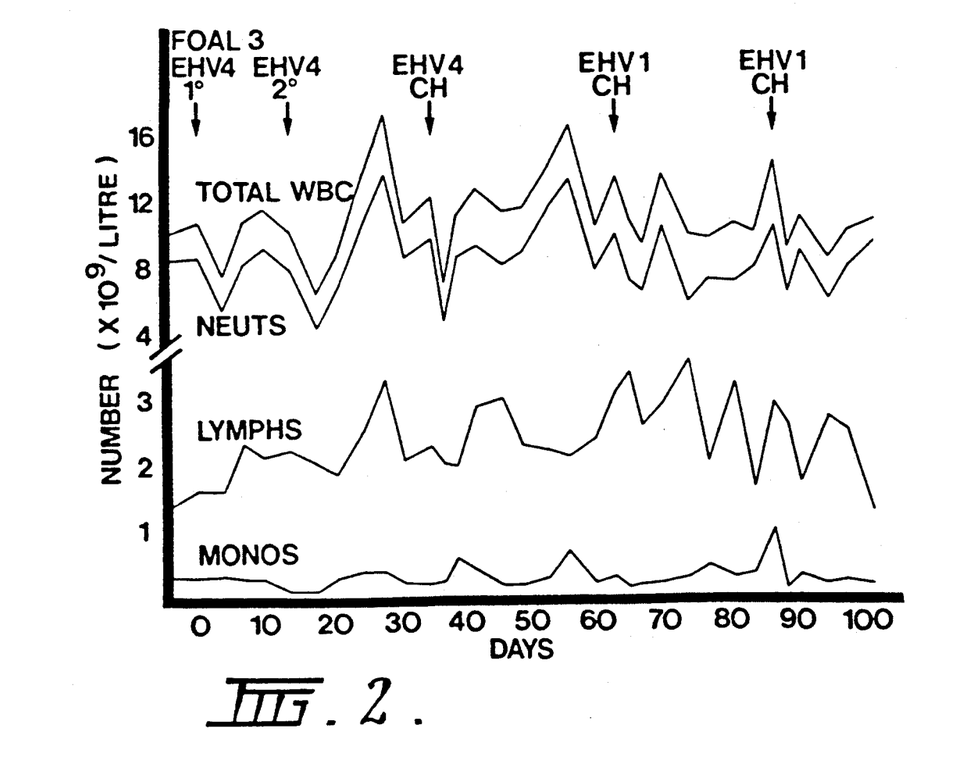
FIG. 2 shows graphs of the total and differential leukocyte counts for foal 3.

Total and differential counts for foal 3 are shown in FIG. 2. Total WBC numbers varied directly with variations in neutrophil numbers. Lymphocyte counts increased after each vaccination and after the first challenge exposure. Later variations in lymphocyte counts could not be accounted for.

Similar changes were observed in foals 1 and 2, although in foal 1, a sharp decrease in lymphocyte count ($2.7 \times 10^9$ cells/L to $1.85 \times 10^9$ cells/L) occurred two days after the first challenge exposure, before a later increase in lymphocyte count at day seven.

Although virus was not isolated from the WBC preparation of any foal, virus was isolated from a single nasal swab-from foal 2 on day 83 (two days after challenge with EHV-4). The virus was typed as EHV-4.

Mononuclear cell suspensions had a median purity of 96% mononuclear cells (n=110), with the main contaminating cells being neutrophils and basophils. Average yield of mononuclear cells from blood samples was 50%. Viability was always >95% at the start of incubation. Repeatability (triplicate wells) was satisfactory with SE approximately 14% of the mean.

Figure 3:
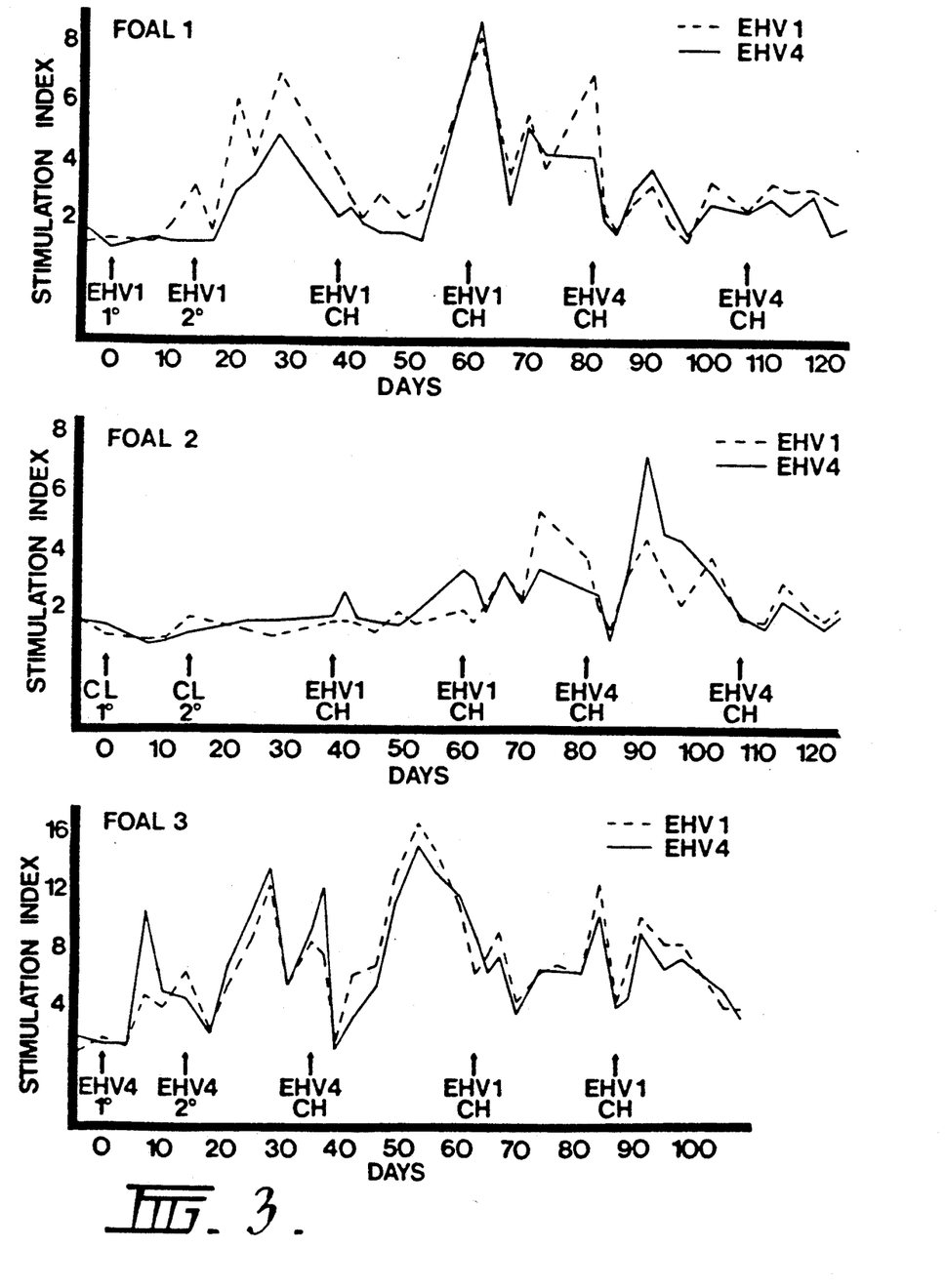
FIG. 3 shows three graphs of the peak lymphocyte blastogenesis responses of three foals to EHV-1 and EHV-4 antigens in vitro.

Peak responses of all foals to EHV-1 Ag and EHV-4 Ag are shown in FIG. 3.

Foal 1 responded in vitro after vaccination with peak SI that initially (days 14 and 21) were specific for the vaccination type (EHV-1) by a factor of 2 or more, but all later peak SI were of similar magnitude to both EHV-1 Ag and EHV-4 Ag, regardless of the type of the virus used in the challenge inoculum and the record of earlier exposure.

Foal 2 did not respond in vitro to either EHV-1 Ag or EHV-4 Ag after vaccination with control CL Ag. The peak SI after challenge exposure tended to favour the type of the challenge virus, but the differences were smaller than those in foal 1.

The response of foal 3 was similar to that of foal 1, i.e. an early response at day 7 was specific for the vaccination type (EHV-4) followed by peak SI of similar magnitude to EHV-1 Ag and EHV-4 Ag during the remainder of the vaccination and challenge exposure periods.

Figure 4:
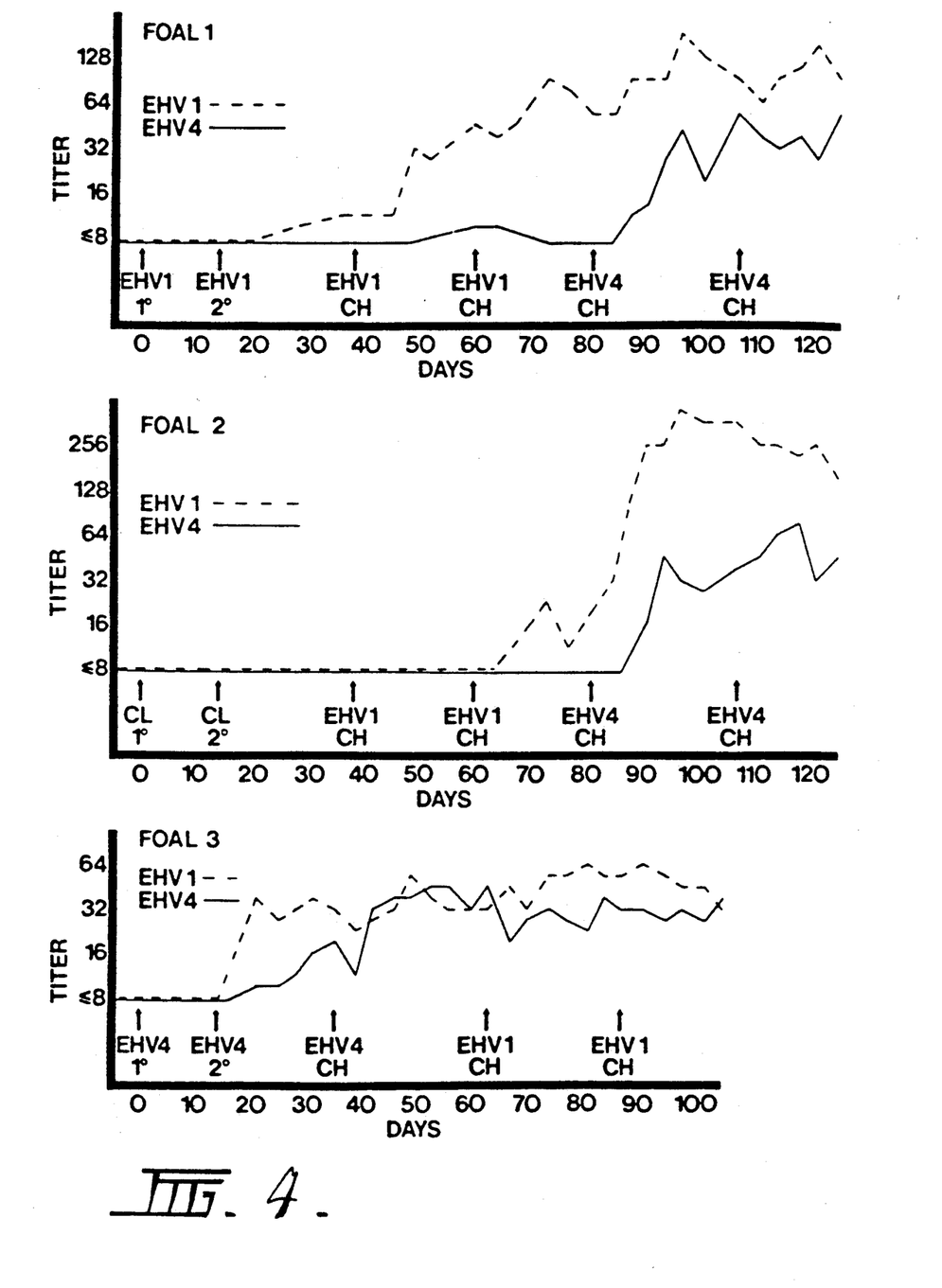
FIG. 4 shows three graphs of the serum virus-neutralizing antibody titers of three foals against EHV-1 and EHV-4.

The VN Ab titers against EHV-1 and EHV-4 for all foal sera are shown in FIG. 4.

Foal 1 produced low concentrations of EHV-1 VN Ab after 2 vaccinations with EHV-1 Ag and these concentrations were increased by 2 EHV-1 challenge exposures to a titer of 90 at day 73. This response to EHV-1 vaccination and challenge exposure was highly specific with only traces (titers $\leq 9$) of EHV-4 VN Ab present up to day 81. Subsequent challenge exposures with EHV-4 on days 81 and 107 increased the titers of both EHV-4 VN Ab and EHV-1 VN Ab.

Foal 2 remained free of detectable VN Ab (titers <8) after two vaccinations with control CL Ag and one challenge exposure with EHV-1. A second EHV-1 challenge exposure on day 60 elicited a small EHV-1 VN Ab response (to a titer of 22 on day 73). Challenge exposure with EHV-4 on day 81 increased the EHV-1 VN Ab to high titers (<256) and elicited detectable EHV-4 VN Ab titers after day 91. The EHV-4 VN Ab titers increased after the second EHV-4 challenge exposure on day 107, whereas EHV-1 VN Ab levels were unaffected.

Foal 3 produced both EHV-1 VN Ab and EHV-4 VN Ab after EHV-4 Ag vaccination, with higher titers of EHV-1 VN Ab. Challenge exposure with EHV-4 increased the levels of both viral Ab to comparable titers of ~38. Subsequent challenge exposures with EHV-1 had little effect on EHV-4 VN Ab titers and produced only slight increases in EHV-1 VN Ab titers.

The VN Ab titers of immunized rabbits against both EHV-1 and EHV-4 are shown in Table 2. Sera from EHV-1 immunized rabbits were highly specific for EHV-1 and showed little cross-reactivity for EHV-4. Sera from EHV-4 immunized rabbits neutralized both EHV-1 and EHV-4 to abut the same titer.

Clinical signs of respiratory tract disease were not observed in any of the three foals. Reduced clinical disease was reported for SPF gnotobiotic foals inoculated intranasally with EHV-1 or EHV-4 and may be due to an atypical microbial flora in the respiratory tract of these foals.

Virus isolation from WBC samples after challenge exposures was unsuccessful, even though several processing techniques were attempted. The EHV-4 was recovered from a nasal swab from foal 2 on day 83 (or 2 days after intranasal EHV-4 challenge exposure) and may represent active infection of a nonimmune foal, but this was not confirmed.

In vitro LB responses to EHV-1 Ag and EHV-4 Ag were used to determine the specificity of a cellular immune response of horses to EHV-1 and EHV-4. Type-specific responses, even though significantly cross-reactive, have been demonstrated for herpes simplex cirus type 1 (HSV-1) and type 2 (HSV-2), using this approach. Except for the early responses of foals 1 and 3 when peak SI after vaccination were specific for the immunizing type of virus by a factor of >2, the peak SI to EHV-1 Ag and EHV-4 Ag were of similar magnitude, regardless of the type of the virus used and regardless of the record of earlier exposure of the foals. For primary HSV-1 infections of persons, a similar pattern with an early type-specific LB response followed by a response cross-reactive to HSV-2 has been described, but generally, the type specificities of the LB responses to HSV-1 and HSV-2 are consistently manifested by at least a 2-fold difference in SI. Such a clear difference was not demonstrated for EHV-1 and EHV-4. Specificity of the cellular immune response of the horse to EHV-1 and EHV-4 may be further characterized by using other assays of cellular immunity.

Foals and rabbits exposed to EHV-1 produced a specific EHV-1 VN Ab response, with little production of EHV-4 VN Ab; animals exposed to EHV-4 produced a cross-reactive response with equivalent titers of EHV-1 VN Ab and EHV-4 VN Ab. This relationship (Tables 2 and 3), using hyperimmune sera from rabbits and foals is similar to other studies, using hyperimmune rabbit antisera and gnotobiotic foal antisera to EHV-1 and EHV-4. FIG. 4 illustrates the maintenance of this relationship during the development of VN Ab in SPF foals after sequential exposure to EHV-1 and EHV-4 or vice versa.

It seems that EHV-1 possesses type-specific antigenic determinant(s), presumably in the envelope glycoproteins, that are important for the generation of VN Ab to this virus, whereas antigenic determinants common to both EHV-1 and EHV-4 are the most significant determinants recognized during the VN Ab response to EHV-4. Further studies with monoclonal antibodies to EHV-1 and EHV-4 and preparations of individual glycoproteins from each type may define this relationship more closely.

Whether EHV-1 and EHV-4 are cross protective in horses remains unclear. The small number of SPF foals used in the present preliminary study, together with the lack of clinical disease and virus isolations after challenge exposure, even from the control foal, prevented making full assessment of cross protection. The 3 SPF foals were, nevertheless, invaluable for determining the specificity of certain immune responses to vaccination and challenge exposure with EHV-1 and EHV-4. Cross-reactive LB responses were demonstrated in all foals after exposure to either EHV-1 or EHV-4 and are noteworthy in comparison to the type-specific responses for HSV-1 and HSV-2.

However, the relative importance of this cellular immune response in vivo and its correlation with resistance to infection are not established. In contrast, the role of antibody in defense against herpesvirus infection both alone and in combination with complement and K cells is recognized, indicating that a highly specific antibody response to EHV-1, as demonstrated in the present experiments, may not cross protect against infection with EHV-4.

The specificity of the antibody response raises questions about the use of vaccines based on EHV-1 alone to control both EHV-1 and EHV-4 infections. Although it is possible that repeated vaccinal doses of EHV-1 may elicit some EHV-4 VN Ab, it would seem more appropriate to use a vaccine derived from EHV-4 to achieve this. This preliminary study indicates that a monovalent EHV-4 vaccine would elicit antibody and cellular immune responses to both EHV-1 and EHV-4. However, it seems more likely that the most appropriate vaccine for the control of abortion and rhinopneumonitis should be vivalent, incorporating both EHV-1 and EHV-4.

I claim:

1. A vaccine based on the equine rhinopneumonitis virus (equine herpesvirus) type 4 (EHV-4) in an inactivated or attenuated live virus form.

2. A combined vaccine based on the equine abortion virus (equine herpesvirus type 1 (EHV-1)) and equine rhinopneumonitis virus (equine herpesvirus type 4 (EHV-4)) in an inactivated or attenuated live virus form.

3. The vaccine of claim 2, wherein EHV-1 and EHV-4 are present in equal proportions.

4. The vaccine of claim 1 or 3 wherein the virus is contained in an adjuvant and a suitable preservative.

5. The vaccine of claim 4, where the adjuvant is aluminum hydroxide.

6. The vaccine of claim 2 or 3, wherein the strains of virus are EHV-1 strain 438/77 and EHV-4 strain 405/76 each having a titre greater than $10^{7.5}$ plaque forming units per ml.

7. A method of vaccinating against the diseases caused by equine herpesviruses comprising injecting intramuscularly or sub-cutaneously an effective quantity of vaccine according to claim 1 or claim 2.

* * * * *

UNITED STATES PATENT AND TRADEMARK OFFICE
CERTIFICATE OF CORRECTION

PATENT NO. : 5,084,271
DATED : January 28, 1992
INVENTOR(S) : Michael J. Studdert Page 1 of 2

It is certified that error appears in the above-indentified patent and that said Letters Patent is hereby corrected as shown below:

Column 3, between lines 39 and 40, insert the following:

--

Table 1
Schedule of Immunizations and Challenges of Specific Pathogen Free Foals with EHV 1 and EHV 4

| Day | Foal 1 | Day | Foal 2 | Day | Foal 3 |
|---|---|---|---|---|---|
| Immunizations | | Immunizations | | Immunizations | |
| 0 | EHV 1 Ag[1] + Adjuvant IM[2] | 0 | CL Ag[3] + Adjuvant IM | 0 | EHV 4 Ag[4] + Adjuvant IM |
| 14 | EHV 1 Ag + Adjuvant IM | 14 | CL Ag + Adjuvant IM | 14 | EHV 4 Ag + Adjuvant IM |
| Challenges | | Challenges | | Challenges | |
| 38 | $10^{6.0}$ PFU[5] EHV 1 IN[6] | 38 | $10^{6.0}$ PFU EHV 1 IN | 35 | $10^{7.5}$ PFU EHV 4 IN |
| 60 | $10^{7.0}$ PFU EHV 1 IN | 60 | $10^{7.0}$ PFU EHV 1 IN | 63 | $10^{7.5}$ PFU EHV 4 IN |
| 81 | $10^{7.5}$ PFU EHV 4 IN | 81 | $10^{7.5}$ PFU EHV 4 IN | 87 | $10^{7.5}$ PFU EHV 1 IN |
| 107 | $10^{7.5}$ PFU EHV 4 IN | 107 | $10^{7.5}$ PFU EHV 4 IN | | |

1 Inactivated EHV 1 antigen
2 Intramuscularly
3 Control cell lysate antigen
4 Inactivated EHV 4 antigen
5 Plaque forming units
6 Intranasally --; Col. 3, line 65, after "blood" insert -- ) --; Col. 6, between lines 26 and 27, insert --

Table 2
Antigenic Relationships Between EHV 1 and EHV 4 Using Rabbit Antisera

| | EHV 1 Antisera | | EHV 4 Antisera | |
|---|---|---|---|---|
| Virus | Rabbit 1 | Rabbit 2 | Rabbit 3 | Rabbit 4 |
| EHV 1 | 640* | 904 | 904 | 226 |
| EHV 4 | <10 | 14 | 320 | 226 |

* Reciprocal of highest serum dilution neutralizing 100 $TCID_{50}$ of virus

--;

UNITED STATES PATENT AND TRADEMARK OFFICE
CERTIFICATE OF CORRECTION

PATENT NO. : 5,084,271
DATED : January 28, 1992
INVENTOR(S) : Michael J. Studdert It is certified that error appears in the above-indentified patent and that said Letters Patent is hereby corrected as shown below:

Col. 8, line 34 (claim 7), after "vaccinating" insert -- a foal, horse or pregnant mare --; Col. 8, line 34 (claim 7), after "diseases" insert -- , abortion and rhinopneumonitis --.

Signed and Sealed this

Fourteenth Day of November, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,084,271
DATED : January 28, 1992
INVENTOR(S) : Michael J. Studdert It is certified that error appears in the above-indentified patent and that said Letters Patent is hereby corrected as shown below:

On the Title page, item [73], --Assignee:The University of Melbourne, Victoria, Australia. --

Signed and Sealed this

Sixteenth Day of January, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,084,271
DATED : January 28, 1992
INVENTOR(S) : Michael J. Studdert It is certified that error appears in the above-indentified patent and that said Letters Patent is hereby corrected as shown below:

Item [30],
Title, page, under Foreign Application Priority Data, "September 11, 1984" should read —November 9, 1984—.

Signed and Sealed this

Twenty-sixth Day of August, 1997

Attest:

BRUCE LEHMAN

*Attesting Officer*   *Commissioner of Patents and Trademarks*

US005084271B1

REEXAMINATION CERTIFICATE (3288th)

United States Patent [19]

Studdert

[11] B1 5,084,271

[45] Certificate Issued   Aug. 5, 1997

[54] VACCINE FOR EQUINE HERPESVIRUS

[75] Inventor: Michael J. Studdert, Balwyn, Australia

[73] Assignee: The University of Melbourne, Parkville, Australia

Reexamination Request:
No. 90/004,306, Jul. 16, 1996

Reexamination Certificate for:
Patent No.: 5,084,271
Issued: Jan. 28, 1992
Appl. No.: 221,640
Filed: Jul. 8, 1988

Certificate of Correction issued Jan. 16, 1996.

Certificate of Correction issued Nov. 14, 1995.

Related U.S. Application Data

[63] Continuation-in-part of Ser. No. 785,661, Oct. 9, 1985, abandoned.

[30] Foreign Application Priority Data

Nov. 1, 1984 [AU] Australia ................................. PG8064

[51] Int. Cl.$^6$ ..................... A61K 39/245; A61K 39/27; A61K 39/12
[52] U.S. Cl. ..................... 424/229.1; 424/278.1; 424/820
[58] Field of Search ..................... 424/229.1, 278.1, 424/820

[56] References Cited

U.S. PATENT DOCUMENTS 3,725,542   4/1973   Mayr et al. ............................. 424/89

OTHER PUBLICATIONS

Fitzpatrick et al., *Immunologic Relationships Between Equine Herpesvirus Type 1 (Equine Abortion Virus) And Type 4 (Equine Rhinopneumonitis Virus)*, American Journal of Veterinary Research, Oct., 1984, pp. 1947–1952.

Mumford, *Problems Associated With Developing An Inactivated EHV–1 Vaccine*, British Equine Veterinary Association, XXth Annual Congress, Sep. 1–4, 1981, abstract of papers, p. 19.

Mumford, *Problems Associated With Developing A Rhinopneumonitis Vaccine*, British Equine Veterinary Association. General Meeting 13th Feb., 1980, abstracts, p. 2.

Campbell, *Immunity To Equine Herpes–Rhino–And Adeno–Viruses And Studies of Immune Deficiency In Arabian Foals*, Thesis. University of Melbourne, 1981.

Campbell, *Immunogenicity Of Equine Herpes–Virus Type 1 (EHV–1) And Equine Rhinovirus Type 1 (ERhV1) Following Inactivation By Betapropiolactone (BPL) And Ultraviolet (UV) Light*, Veterinary Microbiology, 7:535–544, 1982.

Kawakami et al., *Combined Immunizing Effects Of Live And Inactivated Equine Herpes Virus 1 In Horses*, Proc. of the Fourth Inter. Conf. On Equine Infectious Diseases, 1978, pp. 75–78.

Animal Pharm., Issue No. 21, Nov. 19, 1982, pp. 1–4.

Mumford et al., *Virus And Its Relationship To The 'Poor Performance' Syndrome*, Equine Veterinary Journal, 12(1):3–9, (1980).

Studdert, *Restriction Endonuclease DNA Fingerprinting Of Respiratory, Foetal And Perinatal Foal Isolates Of Equine Herpesvirus Type 1*, Archives of Virology, 1983, pp. 249–258.

*The Virus Blamed For Poor Performance*, The Veterinary Record, Sep. 12, 1981, p. 211.

Fitzpatrick, *Immunologic Relationships Between Equine Herpesvirus Type 1 (Equine Abortion Virus) and Type 4 (Equine Rhinopneumonitis)*, Thesis, University of Melbourne, 1984.

*Primary Examiner*—Nathan M. Nutter

[57]   ABSTRACT

A vaccine for equine herpesvirus which includes the equine rhinopneumonitis virus (equine herpesvirus) type 4 (EHV-4) in an inactivated or modified live virus form.

Also disclosed is a combined vaccine based on the equine abortion virus (e.g. herpesvirus type 1 (EHV-1)) and equine rhinopneumonitis virus (equine herpesvirus type 1 (EHV-1)) and equine rhinopneumonitis virus (equine herpesvirus type 4 (EHV-4)) in an inactivated or modified live virus form.

The viruses are present in a suitable adjuvant with a suitable preservative.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–7 is confirmed.

* * * * *